Jan. 15, 1957 E. S. BOERNER Plant Pat. 1,554
CHRYSANTHEMUM PLANT
Filed Feb. 27, 1956
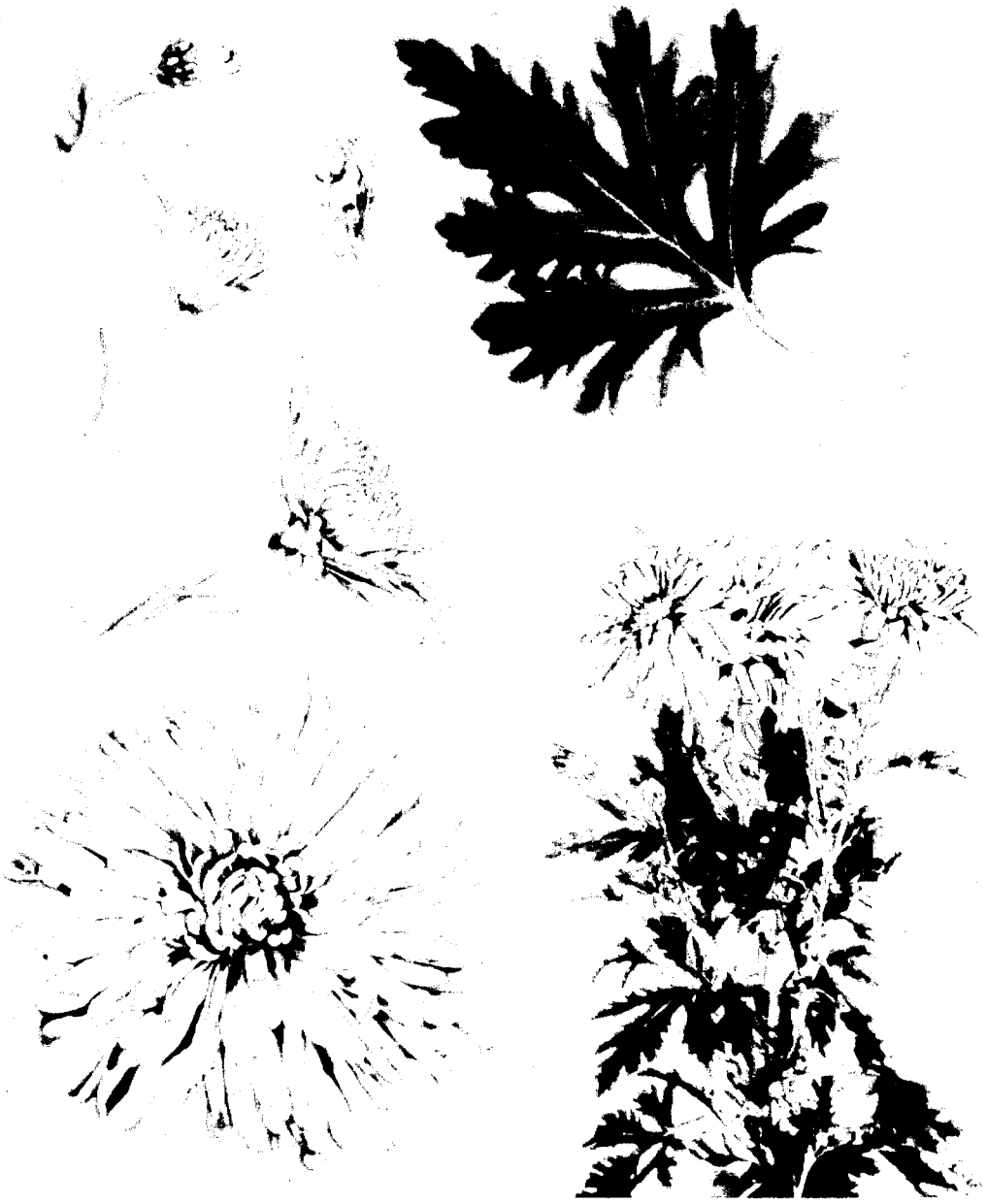
Inventor.
E. S. Boerner
By: Robb & Robb
Attorneys.

United States Patent Office

Plant Pat. 1,554
Patented Jan. 15, 1957

1,554

CHRYSANTHEMUM PLANT

Eugene S. Boerner, Newark, N. Y., assignor to Jackson & Perkins Company, Newark, N. Y., a corporation of New York Application February 27, 1956, Serial No. 568,131

1 Claim. (Cl. 47—60)

The present invention relates to a new and distinct variety of chrysanthemum plant of the semi-decorative type, which was originated by me by crossing the variety "W. F. Snyder" (unpatented) with the variety "Kingbird" (Plant Patent No. 1,306).

The primary objective of this breeding was to produce a new chrysanthemum variety in a pastel Red color never previously attained in chrysanthemums, while at the same time retaining the extreme hardiness which is characteristic of the "Rubellum Kingbird" variety. This objective was fully achieved, together with other improvements and advantages, as evidenced by the fact that my new variety is both vigorous and hardy; its foliage is Light Green in color; and its flowers are Coral Red, lightly overcast with Begonia Rose, in general color tonality.

The foregoing characteristics and distinctions definitely differentiate my new variety from its parents, as well as from all other varieties of its class of which I am aware, and asexual reproduction of the new variety by both top cuttings and underground runners, as performed by me at Newark, New York, shows that these characteristics and distinctions come true to form and are established and transmitted through succeeding propagations.

The accompanying drawing shows typical specimens of the vegetative growth and flowers of my new variety in different stages of development, as well as a typical specimen plant, all as depicted in color as nearly true as it is reasonably possible to make the same in a color illustration of this character.

The following is a detailed description of my new variety, with color terminology in accordance with Ridgway's Color Standards and Nomenclature:

Parentage: "W. F. Snyder" × "Kingbird."
Classification: Semi-decorative type.
Growth: About 3½ feet tall.
Cold resistance: Winter hardy in Northern New York; frost-resistant flowers.

Blooming period: In the Newark, New York, climatic area, blooming begins about October 1st and continues until heavy frosts.

FLOWER (Observations made from specimens grown in a field at Newark, New York, in the early part of October, and in late afternoon.)

Bud:

*Color.*—When petals first divide—Eosine Pink, Plate 1. When petals begin to unfurl—Light Jasper Red, Plate 13. When half-blown: Inside of petals—Spectrum Red, Plate 1, lightly overcast with Rose Doree, Plate 1; outside of petals—Pale Orange Yellow, Plate 3, lightly overcast with Light Jasper Red, Plate 13.

*Peduncle.*—Strong. Color—Light Cress Green, Plate 31.

Bloom:

*Size.*—About 4½ inches.
*Stem.*—Long; normal.
*Form.*—Semi-decorative type.
*Petalage.*—Broad; firm.
*Color.*—Center of flower—Coral Red, Plate 13, lightly overcast with Scarlet Red, Plate 1. Outer petals—Light Coral Red, Plate 13. Base of petals—Clear Dull Green Yellow, Plate 17. Inside of petals—Coral Red, Plate 13, lightly overcast with Begonia Rose, Plate 1. Reverse of petals—Pale Pinkish Buff, Plate 29, with a faint overcast of Geranium Pink, Plate 1.
*Petals.*—Texture—firm; form—oval-pointed.
*Fragrance.*—Characteristic chrysanthemum.

PLANT

Form: Upright.
Growth: Bushy.
Foliage:

*Size.*—Large.
*Quantity.*—Heavy.
*Color.*—Upper side—Forest Green, Plate 17; reverse side—Light Cress Green, Plate 31.
*Texture.*—Smooth.

I claim:

A new and distinct variety of chrysanthemum plant of the semi-decorative type, substantially as herein shown and described, characterized particularly as to novelty by its vigor and hardines, its Light Green foliage, and the distinctive Coral Red, lightly overcast with Begonia Rose, general color tonality of its flowers.

No references cited.